United States Patent [19]
Ruton

[11] Patent Number: 6,155,985
[45] Date of Patent: Dec. 5, 2000

[54] PROCESS FOR DETERMINING THE IMAGE OF THE NASAL AND/OR BUCCAL RESPIRATORY FLOW OF A USER

[75] Inventor: Stephane Ruton, Viroflay, France

[73] Assignee: Taema, Antony Cedex, France

[21] Appl. No.: 09/137,675

[22] Filed: Aug. 21, 1998

[30] Foreign Application Priority Data

Aug. 25, 1997 [FR] France .................................. 97 10605

[51] Int. Cl.[7] ...................................................... A61B 5/08
[52] U.S. Cl. ............................................ 600/529; 600/532
[58] Field of Search ................................ 600/300, 481, 600/500–510, 528–538, 529–532, 534; 128/897–898, 200.14–200.23

[56] References Cited

U.S. PATENT DOCUMENTS

| | | | |
|---|---|---|---|
| 4,905,687 | 3/1990 | Ponkala . | |
| 5,069,222 | 12/1991 | McDonald, Jr. . | |
| 5,353,788 | 10/1994 | Miles | 128/204.23 |
| 5,522,382 | 6/1996 | Sullivan et al. | 128/204.23 |
| 5,792,067 | 8/1998 | Karell | 600/534 |

FOREIGN PATENT DOCUMENTS

| | | |
|---|---|---|
| 0 505 232 | 9/1992 | European Pat. Off. . |
| 0 656 216 | 6/1995 | European Pat. Off. . |
| 0 661 071 | 7/1995 | European Pat. Off. . |
| WO 93/25260 | 12/1993 | WIPO . |

*Primary Examiner*—Cary O'Connor
*Assistant Examiner*—Michael Astorino
*Attorney, Agent, or Firm*—Young & Thompson

[57] ABSTRACT

A process and device to determine the image of the nasal and/or buccal respiratory flow of a user, in which a respiratory gas at at least one pressure level is administered by means of at least one blower driven by a motor. The current consumed by the blower motor is continuously measured and a consumed current signal is generated. The consumed current signal is processed and an image of the nasal and/or buccal respiratory flow of the user is determined from the processed current signal.

9 Claims, 3 Drawing Sheets

PROCESS FOR DETERMINING THE IMAGE OF THE NASAL AND/OR BUCCAL RESPIRATORY FLOW OF A USER

CROSS REFERENCE TO RELATED APPLICATION

This application corresponds to French application 97/10605 of Aug. 25, 1997, the disclosure of which is incorporated herein by reference.

FIELD OF THE INVENTION

The present invention relates to a process and device permitting determining an image of the respiratory flow or flow rate of a user who is likely to be subject to respiratory troubles during sleep, so as particularly to diagnose and/or to treat respiratory troubles, with the help of this image of nasal and/or buccal respiratory flow or flow rate.

BACKGROUND OF THE INVENTION

Respiratory troubles during sleep, such as Sleep Apnea Syndrome (SAS), are characterized in general by disfunction of the respiratory function during sleep.

There is observed in victims subject to such a syndrome, serious interruption of the sleep with short phases of sleep and resumption of normal respiration, accompanied most often by a short waking of several seconds.

The normal course of sleep, from the condition of light sleep to the condition of deep sleep, passing through a condition of paradoxical sleep, is greatly disturbed, which has consequences in the waking hours of these subjects. They thus have the tendency to be sleepy, and to fall asleep while active, and there is also observed in them a decrease of the intellectual and sexual functions, and the risk of hypertension and cardiac insufficiency.

Respiratory troubles can be of the obstructive or central types.

In the first case, there is observed a total obstruction (obstructive apnea) or partial obstruction (obstructive hypopnea) of the upper respiratory tract whilst the muscular strength is maintained. This type of trouble is often associated with loud snoring.

In the second case, muscular control is absent (central apnea) or decreased (central hypopnea), the upper respiratory tract being open.

Obstructive troubles represent the large majority of nocturnal respiratory troubles.

Ordinarily, the diagnosis of respiratory troubles during sleep is carried out in a sleep laboratory, thanks to the recordation and study of numerous interconnected parameters:

during sleep: electroencephalogram, electrooculogram, electro-myogram,
as to cardio-respiratory function: electrocardiogram, respiratory frequency, nasal and/or buccal flow, thoracic and abdominal movements, arterial saturation with oxygen, snoring.

The diagnoses of these sleep pathologies is recent and its use is difficult and requires hospitalization of the subject for one or two nights.

The treatment of sleep respiratory troubles ordinarily uses an apparatus permitting maintaining the upper respiratory tract open.

This apparatus comprises most often a positive pressure apparatus with a mask (CPAP), in which an ambient air compression means, controlled by a control device, delivers into a conduit and then into a mask placed over the nose of the patient in a sealed manner, air under pressure.

The control device compares the value of the pressure in the mask to a reference value of adjusted pressure and, according to the measured difference, adjusts a control signal which it delivers to the ambient air compression means.

At present, the reference value of pressure to be applied in the mask of the patient is determined empirically in the sleep laboratory by progressive increase from an initial reference value, an observation of the consequences on the respiratory troubles, the selected value being the first value for which there is observed uninterrupted normal sleep.

There exist diagnostic and/or treatment devices for these nocturnal respiratory troubles, detecting apnea or hypopnea, but not differentiating between the central and obstructive events.

Other permits, starting from an analysis of the frequency of the pressure signal measured in the mask, detecting snoring and the treatment apparatus thus adjusts the reference value of pressure to suppress snoring.

Still others, after having detected apnea, send to the mask on the patient a pressure impulse and study the possible echo: if there is no echo, the event is central, and if there is an echo, the event is obstructive.

Such apparatus are particularly described in French patents FR-A-2663547 and FR-A-2674133.

However, so as to be able to establish a correct diagnosis of the respiratory troubles (apneas, hypopneas, pathology of increased resistance . . . ) and/or to determine and/or to initiate a suitable and effective treatment, it may be necessary, or even indispensable, that the practitioner, which is to say the doctor or the like, have a reliable image representative of the sequence of the different inhalation and exhalation phases of his patient, which is to say the image of the respiratory flow rate or flow of the subject.

However, the existing processes and apparatus either do not permit such a reliable and effective determination of the image of said respiratory flow rate, or require the use of flow rate detectors, which flow rate detectors cannot be considered as a satisfactory solution, to the extent to which these latter give rise on the one hand to a complication of the overall structure of the apparatus, and hence its size, and, on the other hand, a substantial increase of the cost of the latter.

Moreover, the results obtained with flow rate detectors are not very precise because the latter do not permit taking into account the problem of persons breathing with the mouth open and obtaining a correct image of this nasal respiratory flow.

Thus, a large number of persons suffering from respiratory troubles, in particularly of the obstructive type, have the habit of breathing simultaneously from the nose and from the mouth. However, such buccal respiration appears at present on the nasal respiratory flow image as an apnea, given that it gives rise to an absence of buccal respiratory flow.

Accordingly, it will be easily seen that in similar circumstances, the diagnoses and/or the subsequent treatment can only be incorrect or incomplete.

SUMMARY OF THE INVENTION

The present invention therefore has for its object to provide a process and an apparatus for the diagnosis and/or treatment of sleep respiratory troubles:

not having the drawbacks of known apparatus;
usable both in a sleep laboratory, which is to say in a hospital environment, and at the patient's home;

adapted to permit determining a reliable image of all nasal and/or buccal respiratory flow of a patient, which image is adapted to help in the diagnosis and/or treatment of sleep respiratory troubles, and this in an easy and effective manner;

permitting determining the respiratory flow image of the patient from variations of the current consumed by the motor of the blower supplying the patient with respiratory gas comprising oxygen, such as air;

and which will be of reasonable cost and easy to produce.

The present invention thus relates to a process for determining the image of the nasal and/or buccal respiratory flow of a user, to whom is administered a respiratory gas at at least one pressure level by means of at least one blower driven by a motor, in which:

the current consumed by the blower motor is continuously measured and a consumed current signal is thus derived, the consumed current signal is processed, an image of the nasal and/or buccal respiratory flow of the user is determined from the processed current signal.

As the case may be, the process of the invention can comprise one or more of the following characteristics:

processing of the consumed current signal is carried out by filtering, integration and/or amplification of said signal, there can be a step of memorizing and/or displaying the image of the nasal and/or buccal respiratory flow, the obtained image is the image of nasal or bucco-nasal respiratory flow, there is moreover determined an image of a buccal respiratory flow by means of at least one thermistance, determining the mean value ($V_1$) of the respiratory flow image during a time $t_1$ and the mean value ($V_2$) of the respiratory flow image during a time $t_2$, with $t_1 > t_2$, calculating the value $\Delta(V)$ wherein $\Delta(V) = V_1 - V_2$, deriving the valve $\Delta(V)$ of information concerning the inhalation or exhalation phase, determining the maximum values ($I_{max}$) and minimum values ($I_{min}$) of the flow rate image during a time t corresponding to at least one portion of the duration of a respiratory cycle, determining the amplitude (A) of the image of the flow wherein $A = I_{max} - I_{min}$, comparing the amplitude (A) of the flow rate image with at least one threshold amplitude value (As), also the step of determining from the comparison of amplitude (A) with at least one threshold amplitude value (As), information as to the presence or absence of respiratory trouble, further performing the step of modifying the pressure of the gas delivered by the blower as a function of the result of the comparison of the amplitude (A) with at least one threshold amplitude value (As), setting $t_1$ equal to at least about 5 seconds and preferably to at about 15 seconds and/or $t_2$ is equal to at most about 1 second and preferably at most about 0.125 second.

The invention also relates to a device adapted to practice such a process and in particular a device to determine the image of the nasal and/or buccal respiratory flow of a user, comprising:

means to administer a respiratory gas at at least one level of pressure, comprising at least one blower driven by a motor, supply means comprising at least one conduit for supplying said respiratory gas, connecting the blower to the nasal and/or buccal respiratory passage of the user, means for measuring the current consumed by the blower motor so as to derive a consumed current signal, means for processing said consumed current signal, means for memorizing an image of the nasal and/or buccal respiratory flow of the user.

As the case may be, the device of the invention can comprise one or more of the following characteristics:

the treatment means comprise a filter, an integrator and/or a signal amplifier, it moreover comprises means for processing the image of the respiratory nasal and/or buccal flow of the user, permitting to derive therefrom information as to the presence or absence of respiratory trouble, it is of the type with one or two pressure levels.

The invention moreover relates to the use of such a device and/or such a process for practicing a treatment or diagnostic method of the sleep respiratory troubles of a user and, in particular, for the treatment or the diagnosis of sleep obstructive apnea, hypopnea, and/or of the syndrome of increased resistance of the upper respiratory passages.

DETAILED DESCRIPTION OF THE INVENTION

The present invention is described in more detail hereafter with reference to an embodiment of such a device and to FIGS. 1–6 given by way of illustrative example, but not limiting of the invention.

Figure 1:
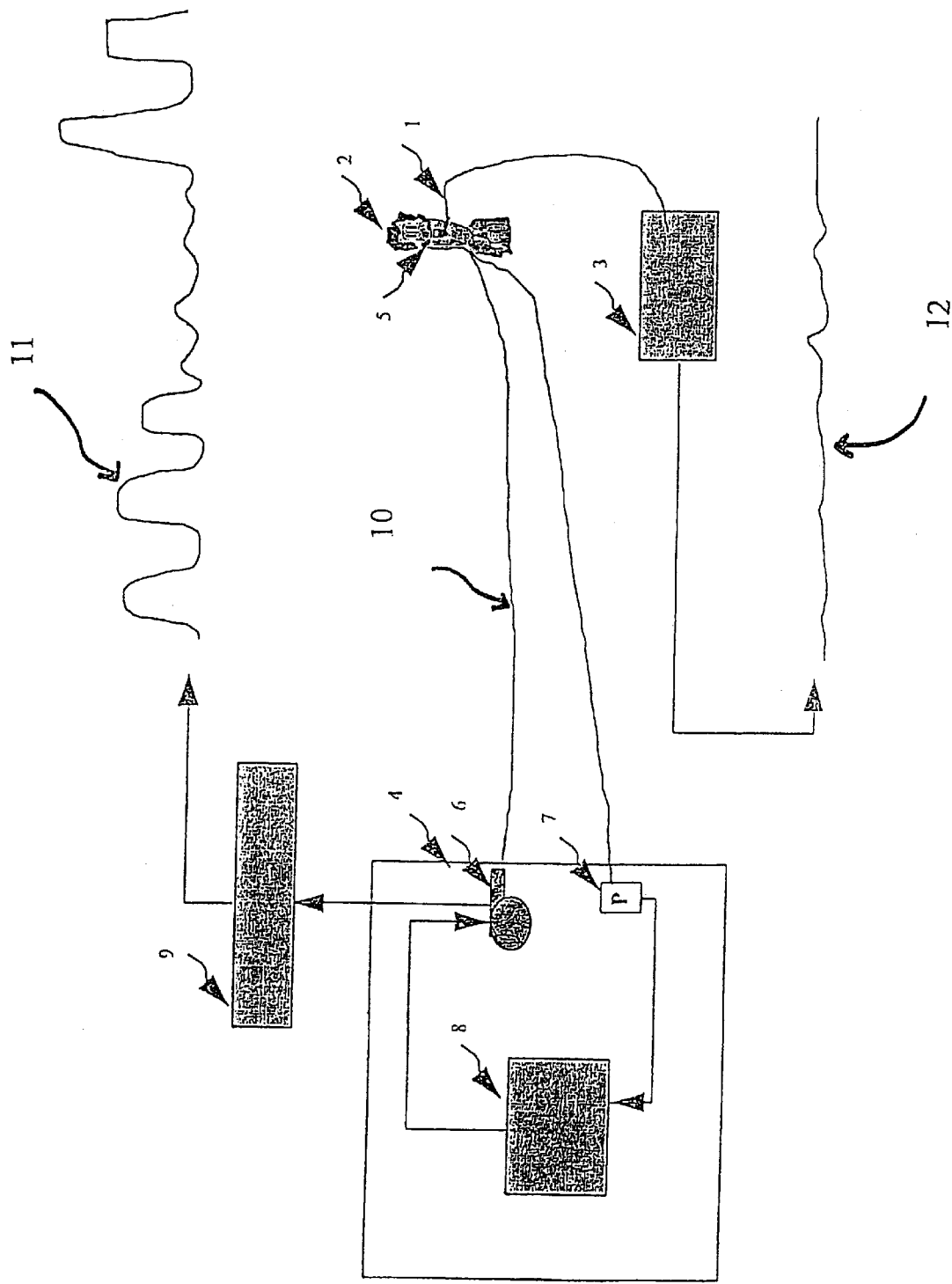
FIG. 1 is a schematic representation of a device using the process of the invention.

FIG. 1 shows the scheme of a device using the process of the invention. More precisely, a user or patient 2 is supplied with respiratory gas containing oxygen, such as air, by a blower 6 actuated by an electric motor (not shown), via a respiratory conduit 10 permitting bringing the respiratory gas under pressure to the respiratory passages of said patient 2.

As the case may be, the respiratory gas is distributed at a positive pressure that is constant with time, which is to say at a single pressure level (CPAP type apparatus), or at a pressure varying between at least one low pressure level and at least one higher pressure level, which is to say with several pressure levels (BPAP type apparatus). The operation of such apparatus having already been described in the prior art, it will not be described in greater detail hereafter. However, for further details, reference could be had particularly to the following documents: U.S. Pat. Nos. 5,492,113 and 5,239,995, EP-A-0 656 216 or EP-A-0 505 232.

The connection between the respiratory conduit 10 and the patient 2 is conventionally carried out by means of a buccal and/or nasal piece 5, such as a mask and/or respiratory earpieces. However, when a nasal piece 5 of the respiratory mask type is used, it is preferable to maintain an over-pressure of gas in this mask: in general between 5 and 20 mbar, for example 12 mbar. Conversely, when a nasal piece 5 of the ear-supported type is used, a slight overpressure of gas (0.20 mbar) suffices.

A pressure detector 7 whose detection point is arranged on the downstream end of the respiratory conduit 10 or on the nasal and/or buccal piece 5, which is to say in immediate adjacency to the respiratory passages of the patient 2, permits detecting pressure variations due to the respiration of the patient, and hence the alternation of the inhalatory and exhalatory phases.

This pressure detector 7 thus transfers, preferably continuously, information on the pressure value to control means 8 of the respiratory flow source, here the blower 6. Preferably, the control means 8 and the blower 6 are inserted in a same housing 4.

This information as to pressure value is then processed by said control means 8, which then supply a control signal to the blower 6 as a function of a reference value of predetermined over-pressure, such as is particularly described in EP-A-0 505 232 or U.S. Pat. No. 5,443,061, so as to modulate the over-pressure supplied by said blower to the patient 2.

It follows that the motor regime of said blower 6 varies as a function of said control signal and hence that the quantity of current consumed by the motor of said blower 6 varies proportionally.

These variations of the current consumed by the motor of the blower 6 are then detected and measured by processing means 9 so as to derive from them a signal representative of the variations of current thus consumed or the signal of current consumed.

This signal of consumed current is then processed by said processing means 9 for the consumed current signal, so as to derive therefrom at least one image 11 representative of the respiratory flow of the user: inhalation phases and exhalation phases and if desired respiratory troubles: apnea, hypopnea, increased resistance . . . .

Figure 2:
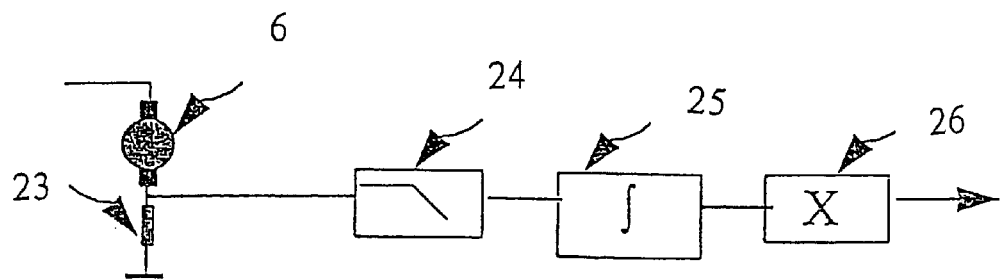
FIG. 2 is a schematic diagram of the processing of a signal representing current consumption by a blower.

As shown schematically in FIG. 2, the processing of the signal of current consumed by the blower 6 comprises the steps of filtering, amplification and/or integration of said signal. This signal processing permits particularly eliminating the major part of the parasitic noise it contains. This processing of the signal can be carried out by means of a short circuit resistance 23 or a shunt resistance of low resistance at the terminals of which is carried out the measurement of the voltage of the current, which is to say of a resistance of at least about 0.05 Ohm, preferably of the order of 0.1 Ohm, of a low pass filter 24, an integrator 25 and a signal amplifier 26.

In other words, it has been discovered in a surprising manner, that it is possible to obtain a reliable image 11 representative of the respiratory flow of the patient by the slope of the detection and of the memorization and/or visualization of the variations of current consumed by the blower 6.

It is thus possible, from this image 11, to establish a diagnosis and/or to prescribe an effective treatment for the patients subject to respiratory troubles, particularly by detecting any periods of apnea or hypopnea from this image 11.

However, when the conduit 10 is connected to the patient by means of a nasal piece, such as respiratory earpieces, by proceeding as described above, in certain cases, it will be possible to determine only an incomplete image of the respiratory flow; in particular, when the patient breaths also by the mouth during sleep.

Accordingly, to obtain a complete image of the respiratory flow of the patient, which is to say of the nasal and buccal flow, there is also carried out a determination of the buccal loss (buccal respiration) by means of detection of the buccal respiratory flow, for example a thermistance 1, arranged adjacent the mouth of the patient 2.

Thus, the thermistance 1 can detect any buccal flow, from the temperature variations which it gives rise to immediately adjacent the mouth. More precisely, the thermistance 1 will undergo a variation of electrical resistance as a function of said temperature variations, thereby creating a buccal respiration signal. This buccal respiration signal is then sent to means 3 for processing the buccal respiration signal which process this signal and permit obtaining from it an image 12. This image 12 of buccal respiration can then be used by the practitioner to diagnose the existence of a buccal flow in the patient and adapted correspondingly to treat the patient by taking account of this buccal respiratory flow.

Figure 3:
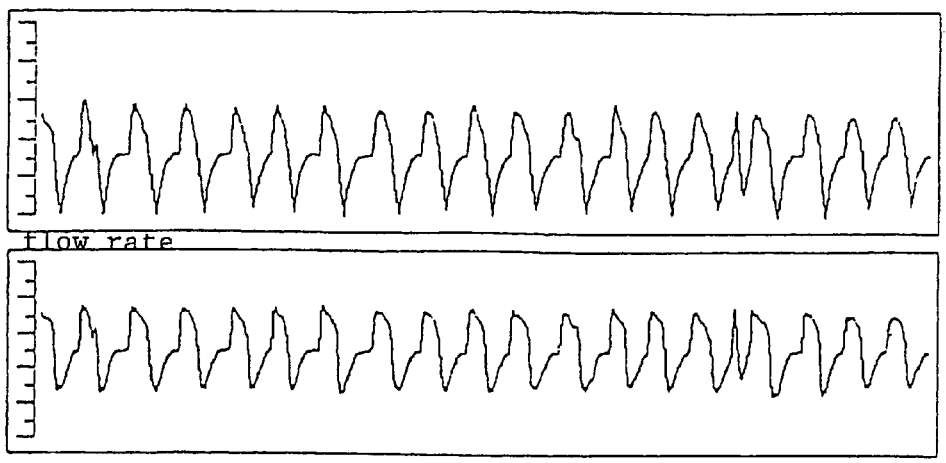
FIGS. 3 to 6 show recordings of the flow rate and the image of the flow rate of a respiratory flow obtained by the present invention.
Figure 4:
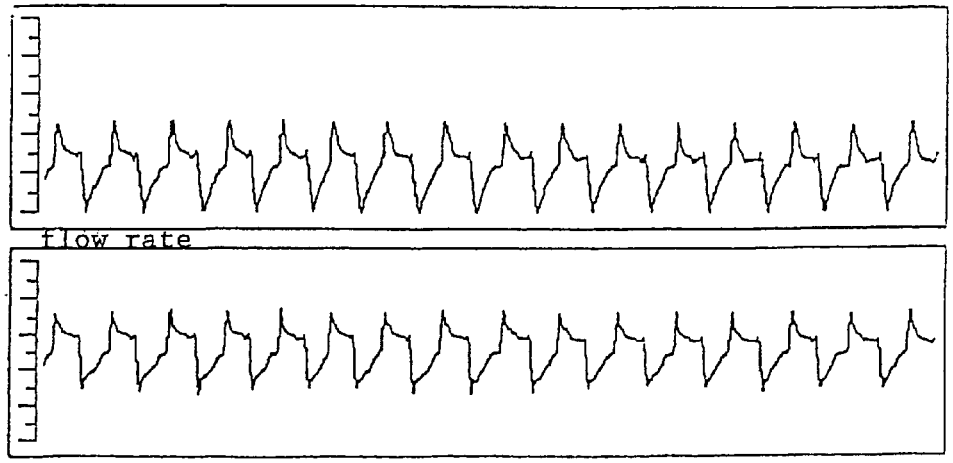
Figure 5:
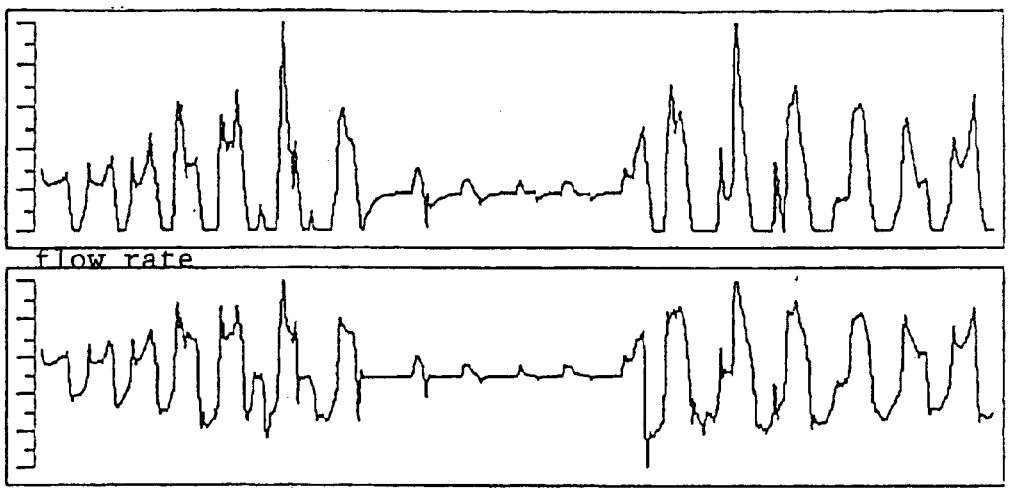
Figure 6:
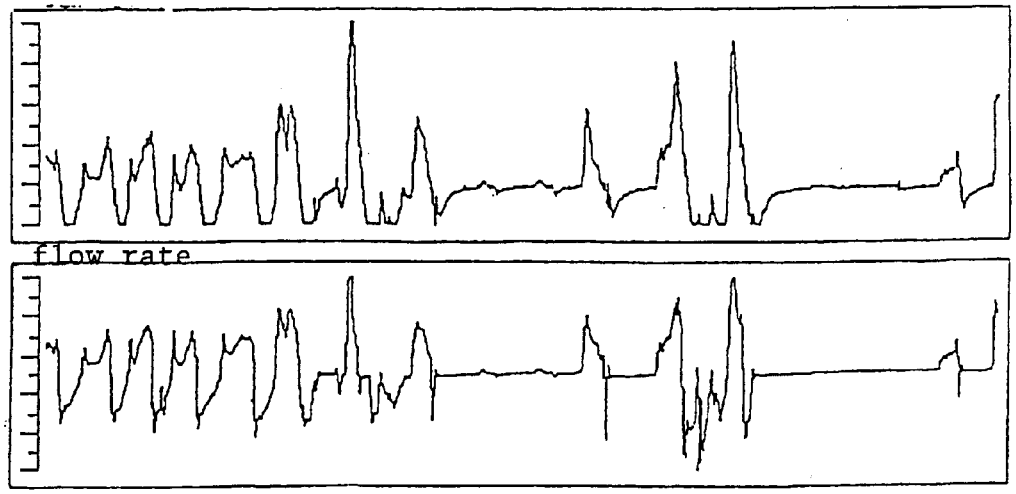

FIGS. 3 to 6 show recordings of the flow rate and the image of the flow rate of a respiratory flow, here a nasal flow, obtained by the process of the invention, the flow rate being measured by means of a pneumotachograph of conventional type. More precisely:

FIG. 3 corresponds to the recordation of normal respiration, which is to say from a patient suffering from no sleep respiratory trouble;

FIG. 4 corresponds to the recordation of respiration at limited flow rate in a patient suffering from increased resistance syndrome of the upper respiratory tract (square shape of the image);

FIG. 5 corresponds to the recordation of respiration with periods of hypopnea;

and FIG. 6 corresponds to the recordation of respiration with periods of apnea.

In all these cases, it is noted however that the image of the flow rate or respiratory flow of the patient obtained by the process of the invention corresponds strictly to the image of current consumed by the blower 6 over the course of time.

From this image, can be determined the mean value $V_1$ of the respiratory flow image during a time $t_1$, for example 25 seconds, and the mean value $V_2$ of the flow image during a time $t_2$ of very much less duration than $t_1$, for example 0.125 second.

There is then calculated the difference $\Delta(V)=V_1-V_2$ for the two mean values $V_1$ and $V_2$ thus determined and there is derived from it information as to the inhalatory or the exhalatory phase, for example:

exhalatory phase when $\Delta(V)>0$; and inhalatory phase when $\Delta(V)<0$.

Thus, the amplitude A of the image of flow rate is determined from the maximum values ($I_{max}$) and minimum values ($I_{min}$) of the flow image during a time t corresponding to at least a portion of a respiratory cycle ($A=I_{max}-I_{min}$) and this amplitude A of the flow rate image is compared with at least one predetermined threshold amplitude value As, so as to derive from it information as to the presence or absence of a respiratory trouble.

For example, if the value of the predetermined threshold amplitude As is a minimum value of normal respiration, then A<As characterizes the presence of a respiratory trouble, for example hypopnea. It is also possible to fix several threshold amplitude values As each representative of a specific respiratory trouble.

From this detection of the presence or absence of respiratory trouble, it is then possible:

either simply to deliver information permitting using the respiratory trouble diagnosis;

or to modify, manually or automatically, the pressure of the gas delivered by the blower, so as to overcome this insufficiency or respiratory trouble by the use of a suitable gas pressure. Manually, this adjustment is carried out by the user or by the practitioner, whilst automatically, this adjustment is carried out by the device itself, which is in autopilot mode.

What is claimed is:

1. A method of determining the image of at least one of the nasal and buccal respiratory flows of a user, comprising:

administering respiratory gas to said user by means of a blower driven by a motor;

continuously measuring the current consumed by the blower motor;

deriving from that measurement a consumed current signal;

processing said consumed current signal;

deriving an image of at least one of the nasal and buccal respiratory flows of the user from the processed current signal;

determining the mean value ($V_1$) of the image of the respiratory flow during a time $t_1$ and the mean value ($V_2$) of the image of respiratory flow during a time $t_2$, wherein $t_1 > t_2$;

calculating the value $\Delta(V)$, wherein $\Delta(V) = V_1 - V_2$; and deriving from the value $\Delta(V)$ information as to the inhalatory phase or the exhalatory phase of the user.

2. The method according to claim 1, and performing the processing of the consumed current signal by at least one of filtering, integration and/or amplification of said signal.

3. The method according to claim 1, which further comprises the step of recording the image of the respiratory flow of the user.

4. The method according to claim 1, wherein the image obtained is the image of buccal respiratory flow.

5. The method according to claim 4, wherein the image of buccal respiratory flow is determined by at least one thermistance.

6. The method according to claim 1, which comprises moreover the steps of determining the maximum value ($I_{max}$) and minimum value ($I_{min}$) of the image of the flow rate during a time t corresponding to at least one portion of the duration of a respiratory cycle; determining the amplitude (A) of the image of the flow rate, wherein $A = I_{max} - I_{min}$; and comparing the amplitude (A) of the image of the flow rate with at least one predetermined threshold amplitude value (As).

7. The method according to claim 6, which further comprises the step of modifying the gas pressure delivered by the blower as a function of the result of the comparison of the amplitude (A) with at least one threshold amplitude value (As).

8. The method according to claim 1, wherein $t_1$ is equal to at least about 5 seconds and $t_2$ is equal to at most about 1 second.

9. The method according to claim 8, wherein $t_1$ is equal to at least about 15 seconds and $t_2$ is equal to at most 0.125 second.

* * * * *